(12) United States Patent
Walsh et al.

(10) Patent No.: US 10,085,861 B2
(45) Date of Patent: Oct. 2, 2018

(54) ENDOLUMINAL DEVICE

(71) Applicant: Boston Scientific Scimed, Inc., Maple Grove, MN (US)

(72) Inventors: Kevin Walsh, Wellesly, MA (US); Gary Trendel, Hopkinton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 117 days.

(21) Appl. No.: 14/533,910

(22) Filed: Nov. 5, 2014

(65) Prior Publication Data

US 2015/0134074 A1 May 14, 2015

Related U.S. Application Data (60) Provisional application No. 61/902,081, filed on Nov. 8, 2013.

(51) Int. Cl.
| | | |
|---|---|---|
| *A61F 2/04* | (2013.01) | |
| *A61F 2/90* | (2013.01) | |
| *A61F 2/86* | (2013.01) | |
| *A61F 2/82* | (2013.01) | |

(52) U.S. Cl.
CPC ............... *A61F 2/90* (2013.01); *A61F 2/04* (2013.01); *A61F 2/86* (2013.01); *A61F 2002/041* (2013.01); *A61F 2002/044* (2013.01); *A61F 2002/045* (2013.01); *A61F 2002/821* (2013.01); *A61F 2210/0014* (2013.01); *A61F 2250/0018* (2013.01); *A61F 2250/0029* (2013.01); *A61F 2250/0039* (2013.01); *A61F 2250/0098* (2013.01)

(58) Field of Classification Search
CPC ...... A61F 2/04; A61F 2/06; A61F 2/82; A61F 2/86; A61F 2/88; A61F 2/885; A61F 2/90; A61F 2002/041; A61F 2002/043; A61F 2002/044; A61F 2002/045; A61F 2002/046; A61F 2002/047; A61F 2002/048; A61F 2002/821
See application file for complete search history.

(56) References Cited

U.S. PATENT DOCUMENTS

| | | |
|---|---|---|
| 5,679,470 A | 10/1997 | Mayer |
| 5,709,703 A | 1/1998 | Lukic et al. |
| 5,800,511 A | 9/1998 | Mayer |
| (Continued) | | |

FOREIGN PATENT DOCUMENTS

| | | |
|---|---|---|
| JP | 2002513627 | 5/2001 |
| JP | 2008519668 | 6/2008 |
| (Continued) | | |

OTHER PUBLICATIONS

PCT International Search Report; PCT International Application No. PCT/US2014/064150 (filed Nov. 5, 2014); dated Feb. 5, 2015; 4 pages.

(Continued)

*Primary Examiner* — Andrew Iwamaye
(74) *Attorney, Agent, or Firm* — Seager, Tufte & Wickhem, LLP (57) ABSTRACT

The present invention relates to an endoluminal device for implantation in a body lumen, such as a pancreatic duct. The device is provided with a distal end region having greater flexibility than that of a medial region of the device.

8 Claims, 11 Drawing Sheets

(56) References Cited

U.S. PATENT DOCUMENTS

| | | |
|---|---|---|
| 6,283,992 B1 | 9/2001 | Hankh et al. |
| 6,379,392 B1 | 4/2002 | Walak |
| 6,533,810 B2 | 3/2003 | Hankh et al. |
| 6,592,549 B2 | 7/2003 | Gerdts et al. |
| 6,723,071 B2 | 4/2004 | Gerdts et al. |
| 6,726,712 B1 | 4/2004 | Raeder-Devens et al. |
| 6,818,015 B2 | 11/2004 | Hankh et al. |
| 7,011,675 B2 | 3/2006 | Hemerick et al. |
| 7,172,617 B2 | 2/2007 | Colgan et al. |
| 7,311,031 B2 | 12/2007 | McCullagh et al. |
| 7,462,192 B2 | 12/2008 | Norton et al. |
| 2003/0135265 A1* | 7/2003 | Stinson ............... A61F 2/90 623/1.16 |
| 2004/0098099 A1* | 5/2004 | McCullagh et al. ......... 623/1.15 |
| 2004/0186549 A1* | 9/2004 | Jayaraman ............ A61F 2/90 623/1.15 |
| 2005/0049682 A1* | 3/2005 | Leanna et al. ............... 623/1.15 |
| 2005/0256563 A1* | 11/2005 | Clerc ................. A61F 2/90 623/1.16 |
| 2012/0083871 A1 | 4/2012 | Ryan |
| 2014/0277371 A1* | 9/2014 | Ryan ................ A61F 2/86 623/1.15 |
| 2014/0277573 A1* | 9/2014 | Gill ................ A61F 2/90 623/23.68 |

FOREIGN PATENT DOCUMENTS

| | | |
|---|---|---|
| JP | 2010279809 | 12/2010 |
| WO | 9956663 | 11/1999 |
| WO | 2006/053270 A2 | 5/2006 |
| WO | 2006053270 A2 | 5/2006 |

OTHER PUBLICATIONS

PCT Written Opinion of the International Searching Authority; PCT International Application No. PCT/US2014/064150 (filed Nov. 5, 2014); dated Feb. 5, 2015; 5 pages.

"Radial Force Testing Equipment," Blockwise Engineering, LLC, Tempe, AZ, 2014; available online at http://www.blockwise.com/radialforce.htm; last accessed on Jan. 27, 2015; 3 pages.

"RX550 (Stents) & RX650 (Filters, Heart Valves, Grafts)," Machine Solutions, Inc., Flagstaff, AZ, 2012; available online at http://www.machinesolutions.com/Medical-Device-Performance-Testing/Testing-Equipment/Radial-Expansion-Force-Testing-Equipment-RX550-650.htm; last accessed on Jan. 27, 2015; 2 pages.

* cited by examiner

ENDOLUMINAL DEVICE

CROSS-REFERENCE TO RELATED APPLICATIONS

This application claims the benefit of U.S. Provisional Application No. 61/902,081, filed Nov. 8, 2013, the entire contents of which are incorporated herein by reference.

FIELD

The present disclosure relates to implantable endoluminal devices such as stents, stent-grafts and similar support devices or frameworks for use in the treatment of various body lumens. In some embodiments, devices of the present disclosure are particularly suited to be advanced from the duodenum and into pancreatic duct so as to prevent narrowing of the duct and/or to restore its patency.

BACKGROUND

Pancreatic endotherapy has been used for years for treatment of several types of pancreatic disorders including but not limited to chronic pancreatitis, idiopathic acute recurrent pancreatitis, and many such others.

Normally, inside the human body the pancreas is connected to the duodenum via the pancreatic duct. The pancreatic duct extends into the duodenum at the major duodenal papilla (adjacent the Ampulla of Vater of the bile duct). The pancreatic duct delivers to the duodenum pancreatic fluids required for metabolism. In various pancreatic disorders, pancreatic tissues may swell or increase abnormally thereby constricting the pancreatic duct and obstructing flow of pancreatic fluids into the duodenum. Such obstructions could lead to various complications including those arising from the accumulation of pancreatic fluids inside the pancreatic tissue or the pancreatic duct. In such cases, an endoluminal device, including a stent or other support structure may be used for treatment of the obstructed pancreatic duct. The endoluminal device provides an outwardly-directed radial force that opens the constriction of the pancreatic duct thereby allowing pancreatic fluid to flow into the duodenum.

Some examples of known devices, their manufacture, and use in treatment of various body lumens including the duodenum and pancreatic duct are shown and described in the following U.S. Pat. Nos. 5,679,470; 5,709,703; 5,800,511; 6,283,992; 6,379,392; 6,533,810; 6,592,549; 6,723,071; 6,726,712; 6,818,015; 7,011,675; 7,172,617; 7,311,031; and 7,462,192. The entire contents of each of these patents being incorporated herein by reference.

Procedures utilizing stents within the pancreatic duct have been performed for several years. Experience has shown that in some cases the pancreatic duct suffers irritation, inflammation, or other complications as a result of the stent's advancement through the duct. A need therefore exists to provide an endoluminal device for use in the pancreatic duct that minimizes or eliminates irritation to the duct tissue during advancement and/or deployment of the device. In some embodiments of the present disclosure a stent is provided with a "soft" distal end or tip which minimizes the forces acting on the pancreatic duct as the endoluminal device is advanced therethrough in order to minimize or eliminate irritation to the duct.

Without limiting the scope of the invention, a brief summary of some of the claimed embodiments of the invention is provided below. Additional details of the summarized embodiments of the invention and/or additional embodiments of the invention can be found in the detailed description of the invention.

All U.S. patents and applications and all other published documents mentioned anywhere in this application are incorporated herein by reference in their entirety.

SUMMARY

The present disclosure describes implantable endoluminal devices for use in body lumens, with particular configurations suitable for the pancreatic duct. In at least one embodiment, the invention is directed to an endoluminal device including a stent. Such devices are provided with a reduced diameter state for advancement into the pancreatic duct and are expandable to an expanded state for secure placement therein. In some embodiments, the stent comprises a self-expandable, braided wire, framework. In at least one embodiment, the device further includes a sleeve. In at least one embodiment, the stent and the sleeve are coextensive along the entire longitudinal length of the endoluminal device. In some embodiments, the sleeve forms at least a portion of the entire outer surface of the endoluminal device. In all embodiments of the endoluminal device a distal end region of the stent is configured with a "soft" tip. The term "soft" refers to the greater flexibility (i.e., relatively reduced force required for radial compression) of the distal end region compared to the main body of the stent. This greater flexibility of the distal end region (compared to the main body of the stent) helps to reduce the radial force acting on the pancreatic duct (and thus minimize irritation thereto) as the endoluminal device is advanced therethrough.

In one or more embodiments an endoluminal device includes a stent, the device having a proximal end region, a distal end region, and a medial region extending therebetween; the distal end region of the device being more flexible than the medial region such that the radial compressive force at a reduced diameter configuration is less at the distal end than the medial region (e.g., radial compressive force at the distal end less than two-thirds of that at the medial region).

In at least one embodiment, an endoluminal device includes a stent (e.g., a stent and a sleeve, etc.), the device having a proximal end region, a distal end region, and a medial region extending therebetween; the distal end region of the device being more flexible than the medial region such that, to radially compress the device to a reduced diameter configuration, the radial compression force required at the distal end region is less than the radial compression force required at the medial region. In some embodiments, the distal end region of the device is more flexible than the medial region such that, to radially compress the device to a reduced diameter configuration, the radial compression force required at the distal end region is less than about two-thirds of the radial compression force required at the medial region.

In at least one embodiment, the stent is constructed from at least one wire, the at least one wire forming a medial region braid pattern in the medial region wherein the at least one wire defines a medial region braid angle (e.g., angle α in, e.g., FIG. 4; an intersection angle that opens toward the proximal end and is located in the medial region) and the at least one wire forming a distal end region braid pattern in the distal end region wherein the at least one wire defines a distal end region braid angle (e.g., angle α' in FIG. 4 or angle α" in FIG. 8; an intersection angle that opens toward the proximal end and is located in the distal end region), the medial region braid angle having a value greater than that of the distal end region braid angle. In at least one embodiment, the distal end region braid angle is a first distal end region braid angle, wherein the at least one wire also defines a second distal region braid angle located more distal than the first distal end region braid angle and having a value less than that of the first distal region braid angle (see, e.g., proximal-facing angle between straight portions 22). In one or more embodiments, the at least one wire also defines a third distal region braid angle located more distal than the second distal end region braid angle and having a value greater than that of the second distal end region braid angle. In one or more embodiments, the median region braid angle is greater than 90 degrees (e.g., greater than 95 degrees, from 95 degrees to 115 degrees, etc.).

In some embodiments, the distal end region of the device includes a plurality of loops formed from the at least one wire, each loop having a length in the axial direction and a width in the circumferential direction, wherein the length is greater than the width. Each loop may include a joining region. For example, each loop may be formed from the at least one wire that includes a first wire and a second wire joined at a joining region. In some embodiments, each loop is interbraided with two adjacent loops. In some embodiments, each loop contacts a single loop in each circumferential direction. In one or more embodiments, each loop is defined by a straight portion that terminates at a distal bend region.

In some embodiments, the at least one wire includes a first wire that extends in a first helical direction in the medial region, transitions into a straight portion that extends in an axial direction in the distal end region, and further transitions into the first helical direction distal of the straight portion. In some embodiments, the first wire further transitions from a first helical direction to a second helical direction, via a bend at the end of the device, the at least one wire further comprises a second wire that extends in the second helical direction and joins the first wire at a joining region.

In some embodiments, the at least one wire includes a first wire that extends in a first helical direction in the medial region, transitions into a straight portion that extends in a generally axial direction in the distal end region, and further defines a first distal curve of about 90 degrees and a second distal curve of about 90 degrees. In one or more embodiments, the first wire further defines a first proximal curve of about 90 degrees, and a second proximal curve of about 90 degrees. In some embodiments, the at least one wire further comprises a second wire that extends in a second helical direction in the medial region, transitions into a straight portion that extends in a generally axial direction in the distal end region, and joins the first wire at a joining region.

In some embodiments of the present disclosure, the distal end region is flared and defines a distal opening that has a greater diameter than the medial region.

In one or more embodiments, an endoluminal device includes a stent (e.g., a stent and a sleeve), the device having a proximal end region, a distal end region, and a medial region extending therebetween; the distal end region of the device being more flexible than the medial region; wherein the distal end region of the device comprises a plurality of loops formed from the at least one wire, wherein each loop is interbraided with two adjacent loops.

In one or more embodiments, an endoluminal device includes a stent (e.g., a stent and a sleeve, wherein the sleeve may be, e.g., a coating, covering, inner tube, outer tube, heat shrink tube, combination of one or more of these, etc.), the device having a proximal end region, a distal end region, and a medial region extending therebetween; the distal end region of the device being more flexible than the medial region; wherein the stent is constructed from at least one wire, wherein the at least one wire comprises a first wire that extends in a first helical direction in the medial region, transitions into a straight portion that extends in an axial direction in the distal end region, and further transitions into the first helical direction distal of the straight portion.

BRIEF DESCRIPTION OF THE FIGURES

The invention and the following detailed description of certain embodiments thereof can be understood with reference to the following figures.

DETAILED DESCRIPTION

While this invention can be embodied in many different forms, specific embodiments of the invention are described in detail herein. This description is an exemplification of the principles of the invention and is not intended to limit the invention to the particular embodiments illustrated.

The invention can be used in humans and used in non-human animals. This invention is suitable for use in the pancreas and for use in other organs and tissues. Although, illustrated embodiments refer to an endoluminal device being placed in the pancreatic duct, the inventive medical device can be used for performing a medical procedure in any body passageway including but not limited to gastro-intestinal tract, the biliary tract, the urinary tract, reproductive tract, the respiratory tract, the arteries and veins. One aspect of the inventive medical device is to expand or open a passageway to allow flow of materials or air inside the body of a patient Various aspects of the invention are depicted in the figures. For the purposes of this disclosure, like reference numerals in the figures shall refer to like features unless otherwise indicated.

As used herein, the terms "proximal" and "distal" are used to indicate and differentiate the end regions of the endoluminal device being described (e.g. a proximal end of the device and a distal end of the device). While it is known that some physicians who regularly utilize pancreatic stents refer to the "distal end" of a pancreatic stent as being that end of the stent which is positioned in (or immediately adjacent to) the duodenum and the "proximal end" of the stent as being that end which is positioned within the pancreatic duct; as used herein however, the term "proximal" refers to an area or portion of the medical device or patient that is closest to the physician during a placement procedure. The term "distal" refers to an area or portion that is farthest from the physician. As used herein, "medial" refers to an area or portion that is disposed between the distal end and the proximal end. In one or more embodiments, the length of the "medial" portion of an endoluminal device divided by the length of the endoluminal device is at least 0.20 (e.g., at least 0.40, at least 0.50, at least 0.60, at least 0.80) and might or might not be centrally located along the length of the endoluminal device.

Figure 1:
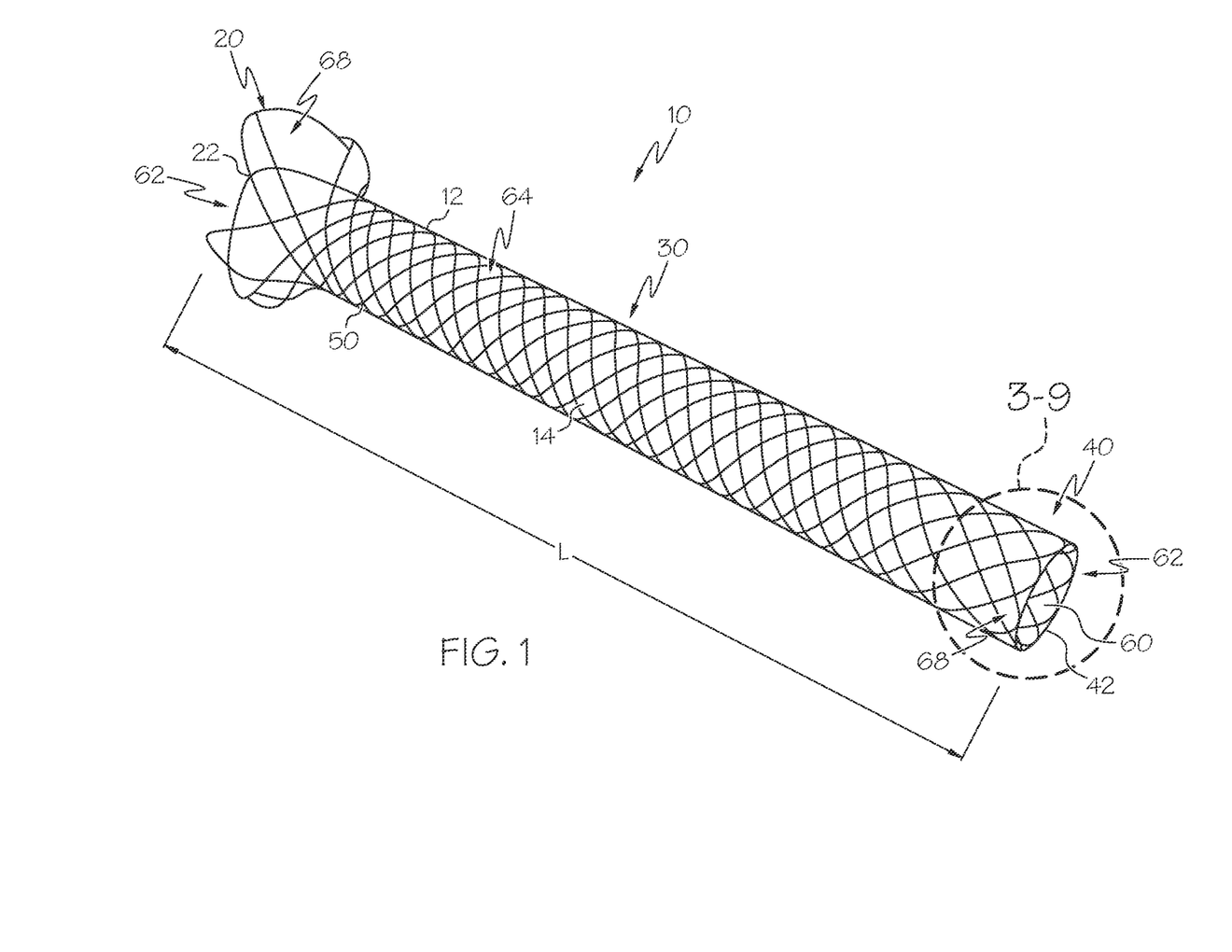
FIG. 1 is a perspective view of an embodiment of the endoluminal device.

Turning to FIG. 1, an endoluminal device 10 is shown. Device 10 is comprised of a stent 12 and a sleeve 14. Device 10 includes an enlarged or flaired proximal end region 20, a distal end region 40, and a medial region 30 extending therebetween. Device 10 has an exterior surface 50 and an interior surface 60. The interior surface 60 defines a passage or lumen 62 which extends between a proximal opening 22 at the proximal end of the device 10 and a distal opening 42 at the distal end of the device 10. The distance between the proximal opening 22 and distal opening 42 defines the device length (L).

As is known in the art, stents such as stent 12 shown, have a plurality of cells or openings along the length and circumference of the stent. These cells or openings are defined by a plurality of structural members. Structural members of a stent depend upon the construction of the stent and include for example, struts, connectors, and wires. Herein, a stent may be constructed or formed from one piece of material (e.g., a wire, a filament, etc.) or may include a plurality of pieces of material (e.g., a plurality of wires and/or filaments, etc.). For example, a plurality of wires may include wires that are bent (e.g., at midpoint, etc.) and woven. As shown and described herein, stent 12 includes spaces or openings 64 that are defined by wires 16, which form the stent 12. In some embodiments, the stent 12 is provided with a retrieval loop (not shown). In other embodiments, one or more of the loops 68 (openings at an end of the stent) which comprise the proximal end region 20 of the stent 12, function as a retrieval loop. The retrieval loop is a means by which the endoluminal device 10, or a portion or portions thereof, can be repositioned or removed after implantation.

Non-limiting examples of suitable materials from which the stent 12 can be constructed from biocompatible materials including one or more polymers, one or more metals or combinations of polymer(s) and metal(s). Polymers that may be used include polyester and polycarbonate copolymers. Examples of suitable metals include, but are not limited to, titanium, tantalum, platinum, tungsten, gold and alloys of any of the above-mentioned metals. Examples of suitable alloys include stainless steel, platinum-iridium alloys, cobalt-chromium alloys including Elgiloy and Phynox, MP35N alloy and nickel-titanium alloys, for example, Nitinol. It is within the scope of the invention for the stent 12 to be self-expandable, balloon expandable, or both balloon expandable and self-expandable.

In some embodiments stent 12 is made of shape memory materials, such as superelastic Nitinol, or may be made of materials which are plastically deformable. In the case of shape memory materials, the stent may be provided with a memorized shape and then deformed to a reduced diameter shape. The stent may restore itself to its memorized shape upon being heated to a transition temperature and/or having any restraints removed therefrom. In some embodiments, a shape memory material does not require heat after it is set the first time.

In some embodiments the stent 12, the delivery system (not shown) or other portion of the endoluminal device 10 may include one or more areas, bands, coatings, members, etc. that is (are) detectable by imaging modalities such as X-Ray, MRI, ultrasound, etc. In some embodiments at least a portion of the endoluminal device 10 is at least partially radiopaque.

In some embodiments of the endoluminal device 10, the stent 12 and/or the sleeve 14 include a therapeutic coating and/or a therapeutic substance delivery mechanism.

In at least one embodiment sleeve 14 is an elastic or conforming polymeric covering. The sleeve 14 can be made of a material that is impermeable, semi-permeable, selectively permeable, permeable, and any combination thereof. Materials that can be used to make the sleeve 14, or sleeve composition, include but are not limited to, silicone, polystyrene-polyisobutylene-polystyrene triblock copolymer (SIBS), polyurethane, polyethylene terephthalate (PET), expanded polytetrafluoroethylene (ePTFE), and any combination thereof. Herein, a sleeve 14 may be applied to a stent 12 by any of a wide variety of methods (e.g., dipping, spraying, coating, wrapping, shrinking, adhering, bonding, friction fitting, etc.) and may be applied to the inside of a stent, the outside of a stent, or both the inside and outside of a stent.

In at least one embodiment, such as is shown in FIG. 1, the stent 12 and sleeve 14 are coextensive along the entire longitudinal length of the endoluminal device 10. In this embodiment, the length of the stent 12 and the length of the sleeve 14 are the same length and equal to the length of the endoluminal device 10. In one embodiment, the stent 12 is disposed within the sleeve 14. In another embodiment, the stent 12 is disposed about (e.g., outside, around, circumscribing, surrounding, etc.) the sleeve 14. When the sleeve 14 is disposed within or about the stent 12, the sleeve 14 covers the openings 64 of the stent 12 so that there are no openings in the wall of the endoluminal device 10. In some embodiments, selected regions or areas of the sleeve 14 define openings to allow branches of the pancreatic duct access to the lumen 62 when the endoluminal device 10 is placed therein. In some embodiments, the sleeve 14 forms at least a portion of the entire outer surface 50 of the endoluminal device 10. In other embodiments, the sleeve 14 forms at least a portion of the entire inner surface 60 of the endoluminal device 10. In still other embodiments, the stent 12 is sandwiched between multiple layers of sleeve material, of which the layers may or may not be of the same material and/or construction.

Figure 2:
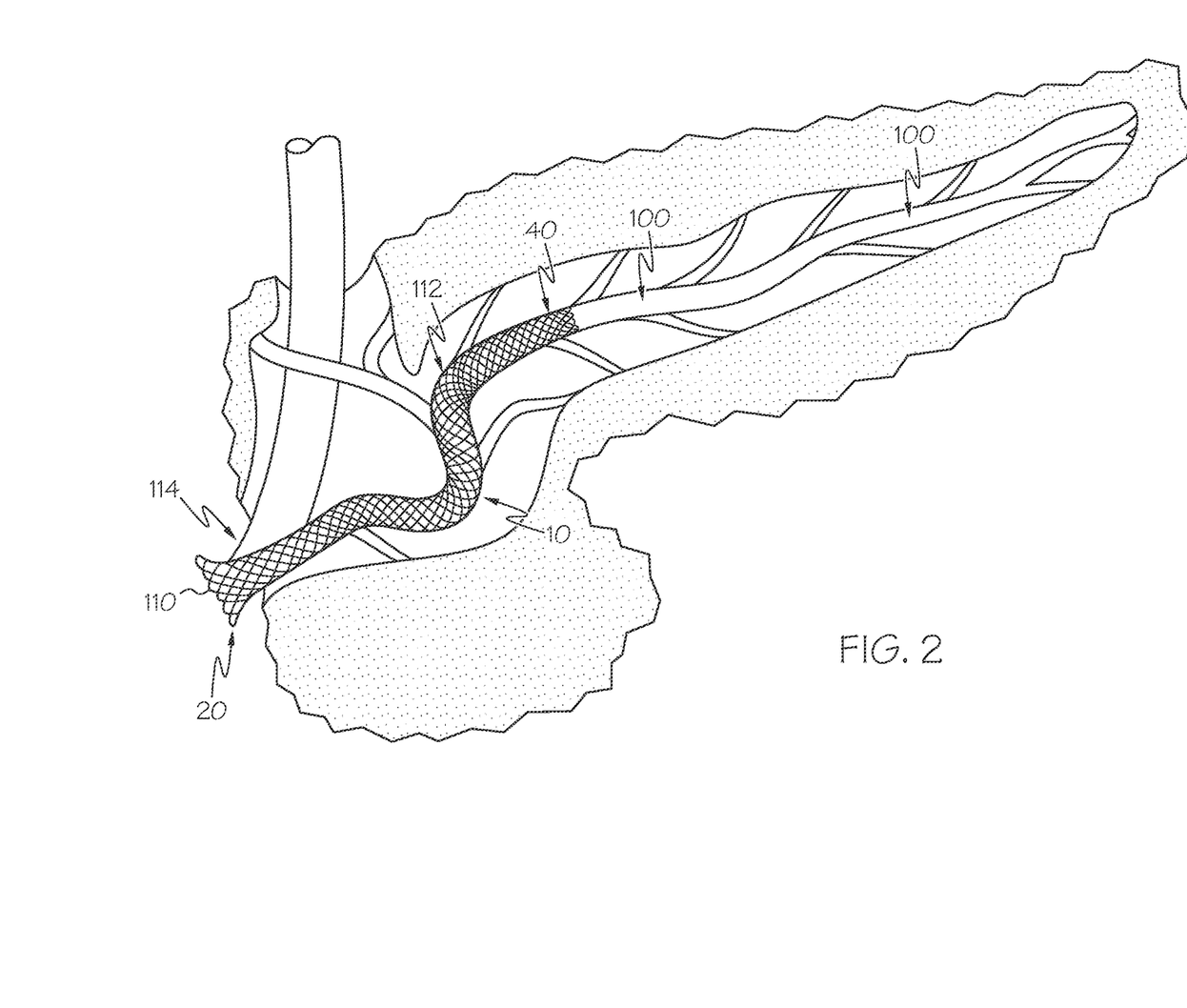
FIG. 2 is an anatomical view of the endoluminal device operationally positioned in a body of a patient.

Turning to FIG. 2 an example of the endoluminal device 10 is depicted following deployment of the device into the pancreatic duct 100. As can be seen, the distal end region 40 is extended well within the pancreatic duct 100. In some embodiments the device 10 is positioned beyond the genu (bend) 112 of the duct or before it. In all cases the flared proximal end region 20 remains within the duodenum 110, abutting the major duodenal papilla 114. As is apparent from the provided illustration the pancreatic duct 100 defines a tortuous pathway through which the endoluminal device 10 must be advanced if it is to be positioned and deployed in the manner shown. It is known that when many prior art devices are advanced through the duct 100, the distal tip of such devices will rub or scrape against, the walls of the genu 112 (as well as other areas of the duct), causing potential irritation and possibly worse complications. Embodiments of the present device 10 shown in FIGS. 3-9 provide the stent 12 with distal end regions 40 with improved flexibility and functional "softness" to minimize or eliminate such irritation.

Figure 3:
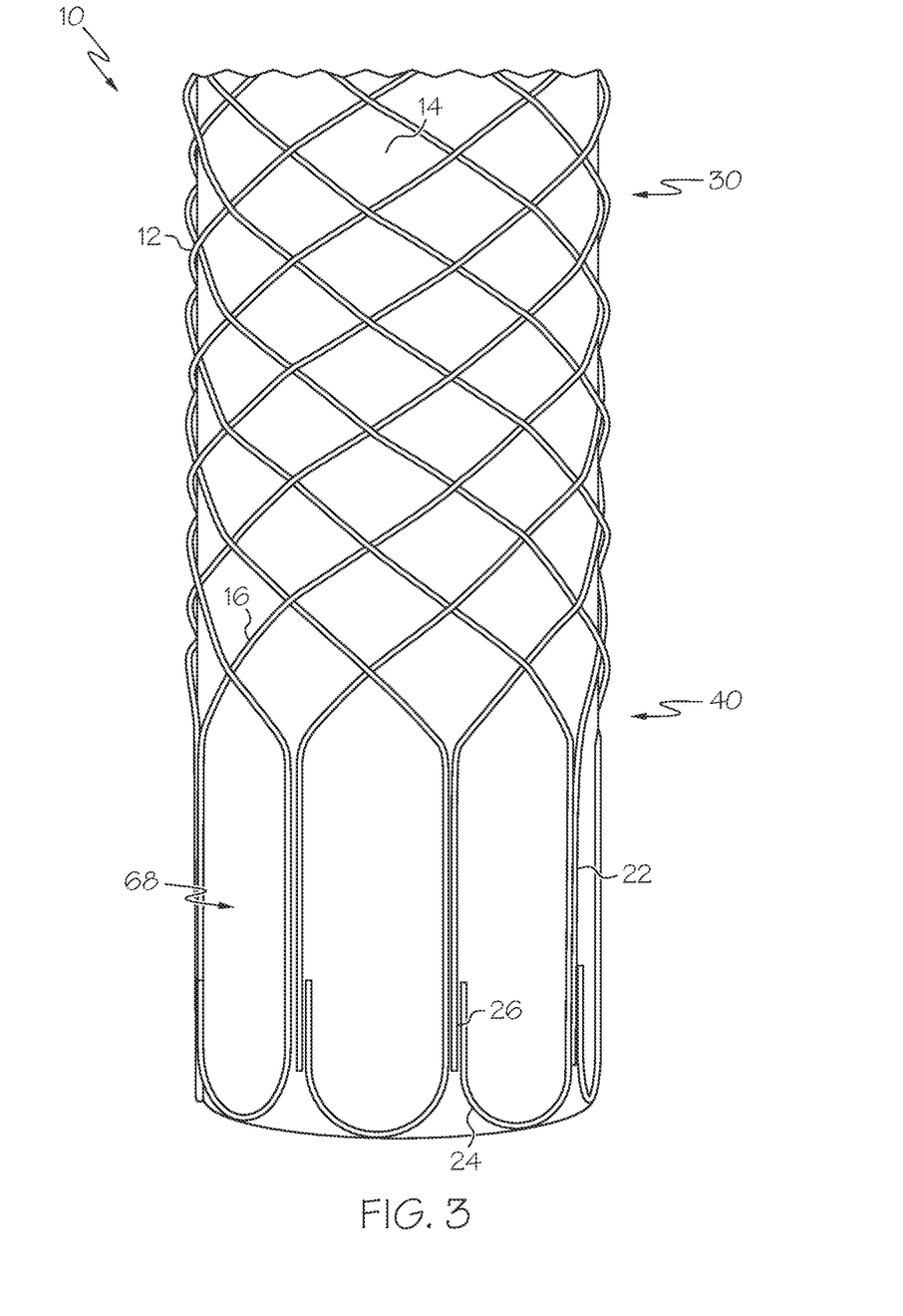
FIG. 3 is an enlarged view of the distal end region of an embodiment of the endoluminal device.

A first embodiment of the stent 12 having an improved distal end region 40 is shown in FIG. 3. In the embodiment shown, the distal end region includes a plurality of loops 68. Each loop 68 is defined by a straight portion 22 of a stent wire 16, which extends from the braid pattern of the medial region 30 (in a first helical direction) into the loop 68. Each straight portion 22 terminates at a distal bend region 24, which bends back from the straight portion 22 toward the medial region 30 of the stent in an approximately 180-degree arc. The wire 16 defining a specific loop 68 terminates at a joining region 26 with an immediately adjacent stent wire 16, which includes a straight portion and extends from the braid pattern of the medial region 30 in a second helical direction. As shown in FIG. 3, each loop has a length in the axial direction that is greater than the loop's width in the circumferential direction.

Figure 4:
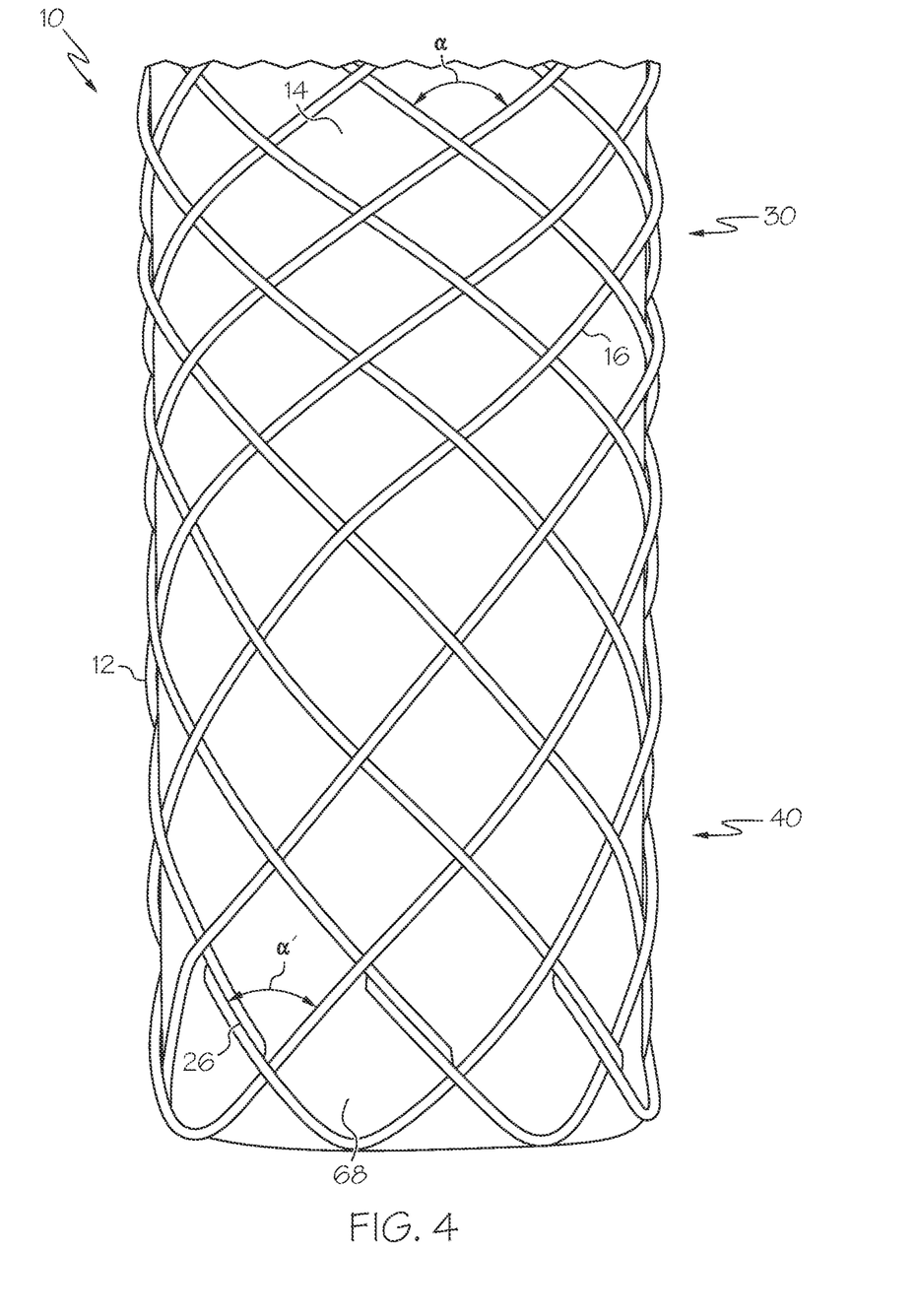
FIG. 4 is an enlarged view of the distal end region of an embodiment of the endoluminal device.

Another embodiment of the stent 12 is shown in FIG. 4. In the embodiment depicted, the stent wire or wires 16 the medial region 30 define a medial region braid angle $\alpha$ of greater than 90 degrees. The term braid angle as used herein refers to the angle made by two wires, or sections of wires and form an angle that opens along the longitudinal axis (e.g., opening in a proximal direction) of the stent. In some embodiments, braid angle $\alpha$ is between 95 and 115 degrees. As the wires 16 extend distally and transition from the medial region 30 to the distal end region 40, the value of the braid angle $\alpha$ is reduced such that at least one (e.g., a plurality of, at least 50 percent of, all of, etc.) all of the braid angles within the distal end region, represented by $\alpha'$, are less than $\alpha$ (e.g., before and/or after deployment). At the distal most end of the stent 12, the wire or wires 16 are bent back proximally in to engage an immediately adjacent wire 16 at a joining region 26 to define end loops 68. In regard to the particular braid angles $\alpha$ and $\alpha'$, the presence of decreasing angles from the medial region 30 to the distal end region 40 is one embodiment of the device 10. Alternatively, the braid angles in the medial region 30 can be the same or different than the angles in the distal end region 40.

Figure 5:
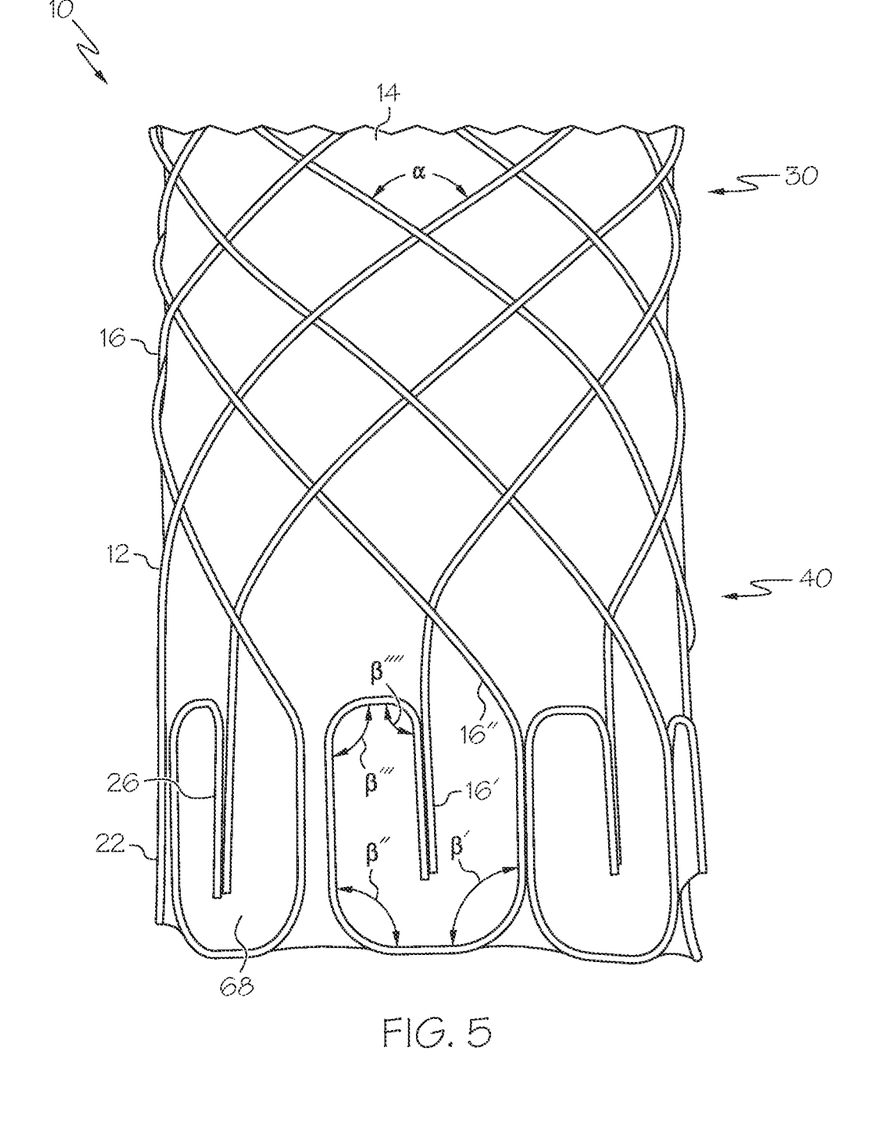
FIG. 5 is an enlarged view of the distal end region of an embodiment of the endoluminal device.

Another embodiment of the stent 12 is shown in FIG. 5. In the embodiment shown, the wire or wires 16 define end loops 68 which have a "G" shape. As in the embodiment shown in FIG. 4, the braid angle $\alpha$ of the stent medial region 30 wire intersections (e.g., between wire 16' extending in a first helical direction and wire 16" extending in a second helical direction) are greater than those of the distal end region 40 ($\alpha'$). In the embodiment shown in FIG. 5 however the loops 68 are formed by joining a straight portions 22 (e.g., extending in an axial direction) of a first wire 16' with an adjacent wire 16". Wire 16" defines a first distal curve $\beta'$ of about 90 degrees, a second distal curve $\beta''$ of about 90 degrees, a first proximal curve $\beta'''$ of about 90 degrees, and a second proximal curve $\beta''''$ of about 90 degrees. Whereupon the straight portion 22 of the first wire 16' and a straight portion 22 of the adjacent wire 16" are joined at a joining region 26.

Figure 6:
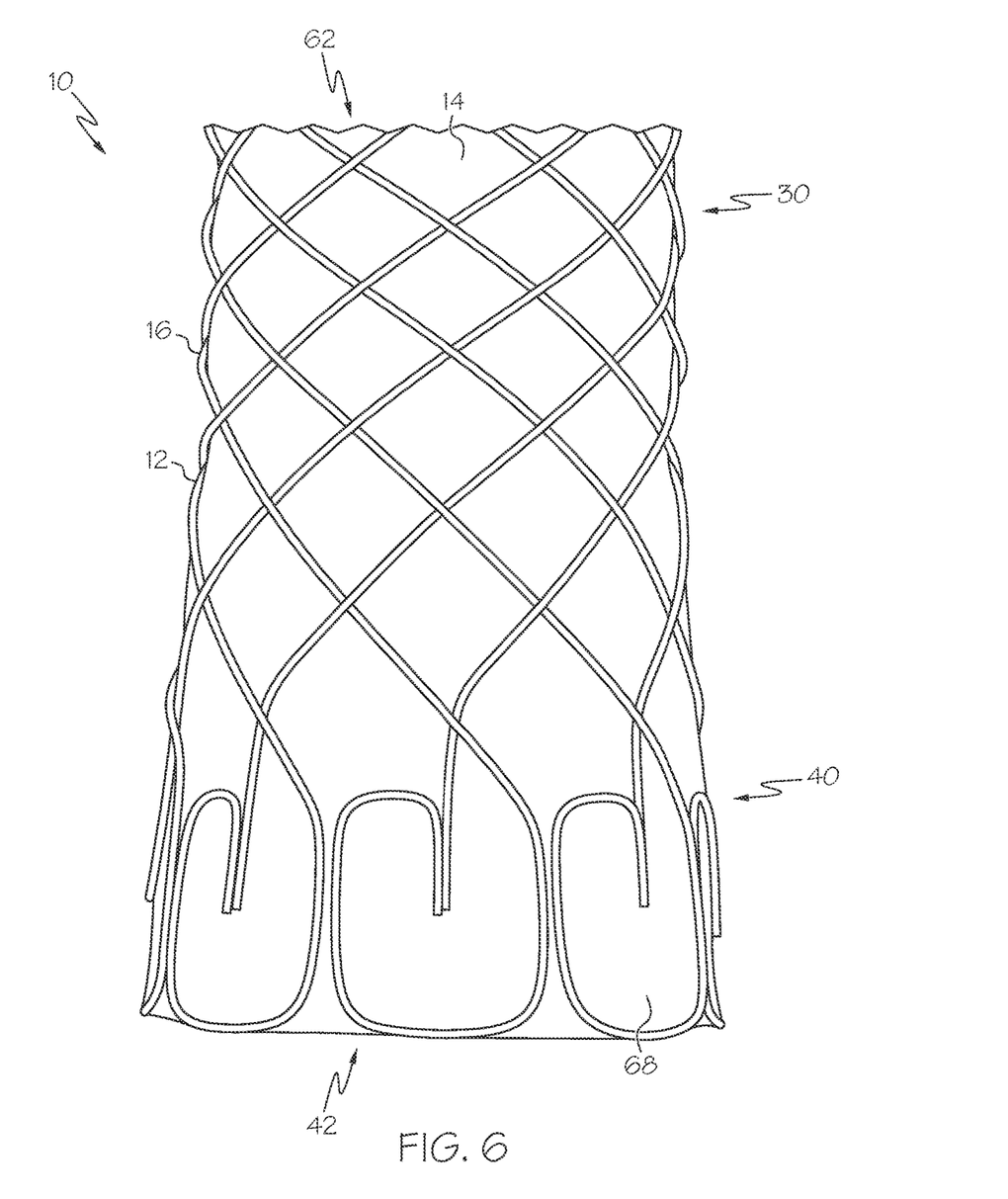
FIG. 6 is an enlarged view of the distal end region of an embodiment of the endoluminal device.

Yet another embodiment of the stent 12 is shown in FIG. 6. In this embodiment, the wire arrangement of the distal end region 40 is the same as that of the embodiment shown in FIG. 5, but the distal end region 40 is flared such that the distal opening 42 has a diameter greater than the diameter of the lumen 62 of the medial region 30.

Figure 7:
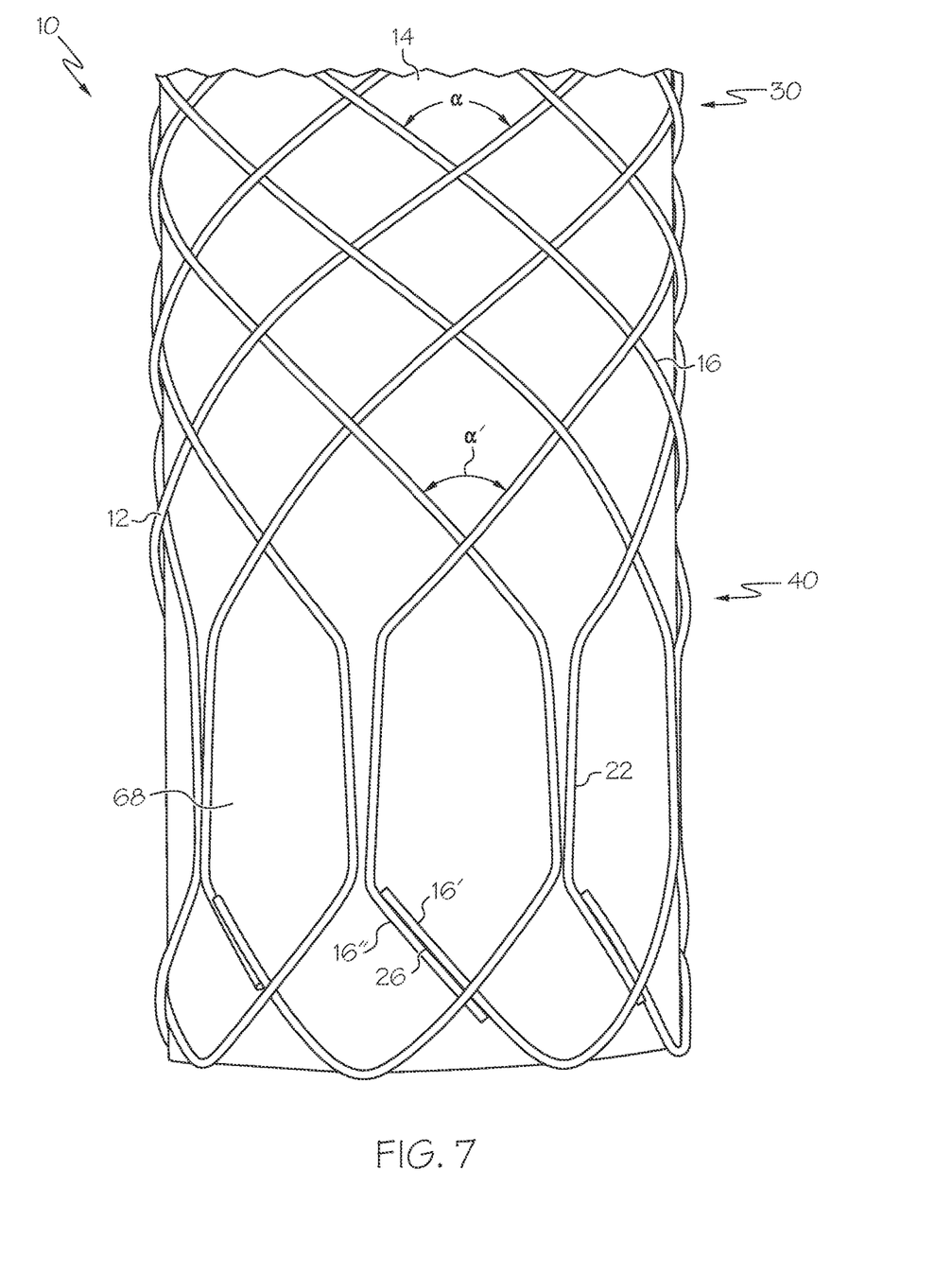
FIG. 7 is an enlarged view of the distal end region of an embodiment of the endoluminal device.
Figure 8:
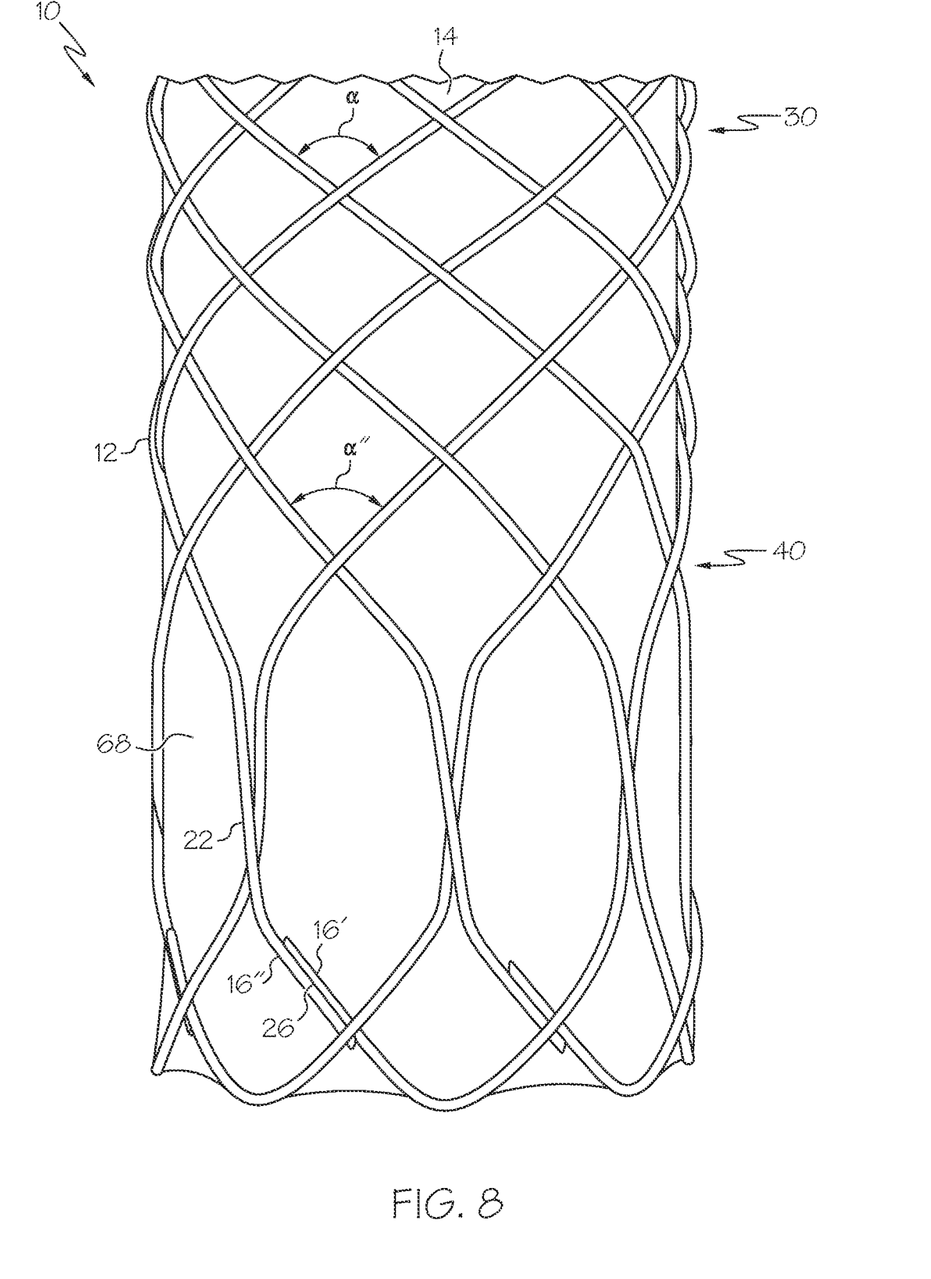
FIG. 8 is an enlarged view of the distal end region of an embodiment of the endoluminal device.
Figure 9:
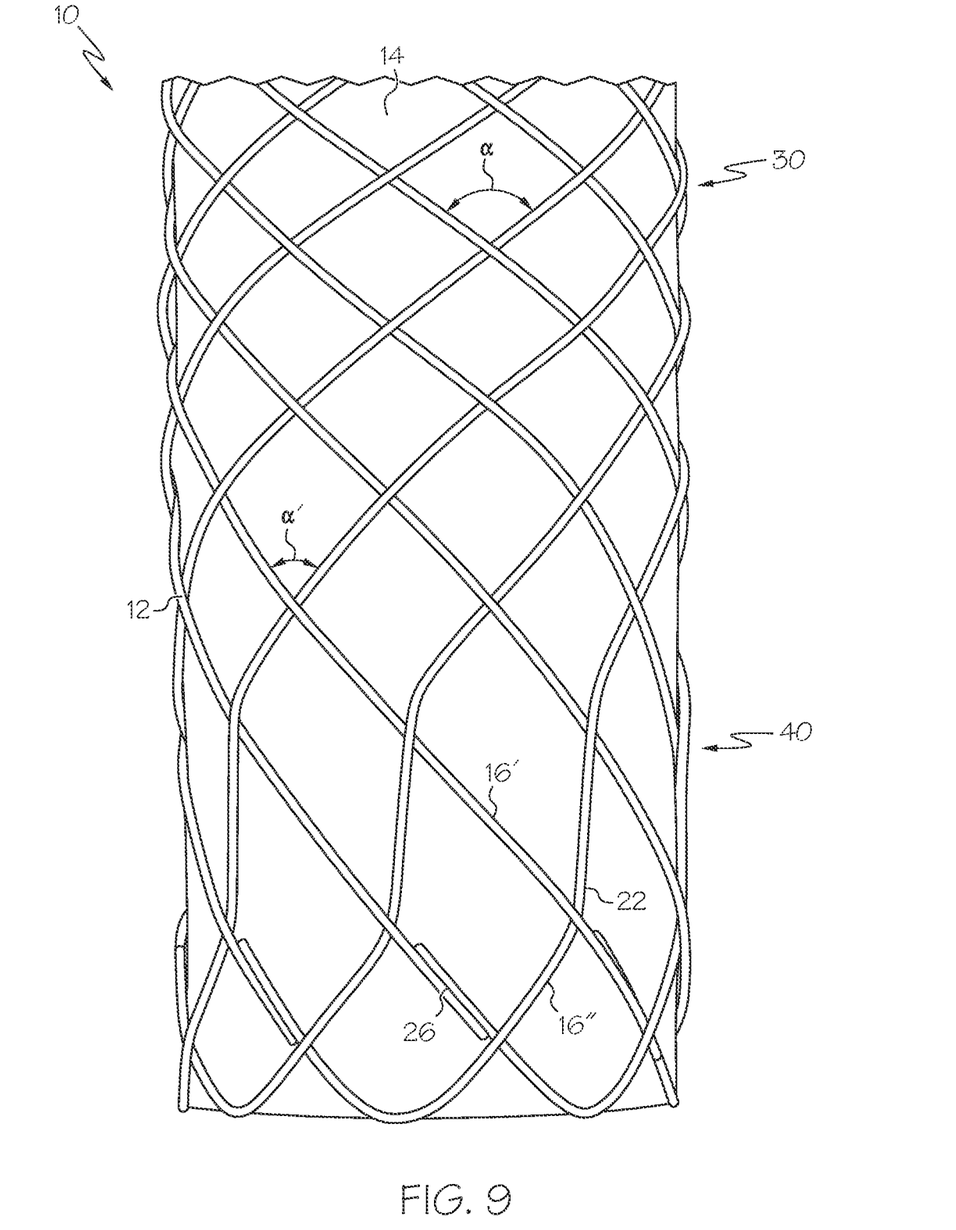
FIG. 9 is an enlarged view of the distal end region of an embodiment of the endoluminal device.

Another embodiment of the stent 12 is shown in FIG. 7. In this embodiment, the braid angles $\alpha$ of the medial region 30 once again transition to smaller braid angles $\alpha'$ in the distal end region 40. Within the distal end region 40 the wires 16 form the loops 68 (e.g., closed loops) with straight portions 22 and which terminate by bending a wire 16' back to join an adjacent wire 16" at a joining region 26. The overlapping of the wire 16 is skipped between straight portions 22 to ensure that there is no contact between the straight portions 22 of adjacent loops 68. In FIG. 7, each loop 68 is shown to overlap, contact, and be loosely linked to (e.g., interbraided with) a circumferentially adjacent loop 68 in each circumferential direction. However, the extent of overlap of loops 68 is such that there is no contact between the straight portions 22. As an alternative to this configuration, the straight portions 22 are made to alternatingly overlap such as in the embodiment shown in FIG. 8. In FIG. 7, wire 16' is shown to extend in a first helical direction (e.g., clockwise) in the medial region, transition into a straight portion that extends in a generally axial direction in the distal end region, transition into a second helical direction (e.g., counter clockwise) distal of the straight portion, and transition at the distal opening into the first helical direction (e.g., clockwise) via a distal bend region. In FIG. 8, wire 16' is shown to extend in a first helical direction (e.g., clockwise) in the medial region, transition into a straight portion that extends in a generally axial direction in the distal end region (where it overlaps a straight portion 22 of a different wire at a second distal region braid angle that is less than the first distal region braid angle that is located proximal of the second distal region braid angle), transition back into the first helical direction (e.g., clockwise) distal of the straight portion (where it overlaps a wire extending in the second helical direction (e.g., counter clockwise) at a third distal region braid angle that is greater than the second distal region braid angle that is located proximal of the third distal region braid angle), and transition at the distal opening into a second helical direction (e.g., counter clockwise) via a distal bend region.

In a final embodiment shown in FIG. 9, again the braid angles $\alpha$ of the medial region 30 transition to smaller braid angles $\alpha'$ in the distal end region 40. The geometry of the distal end region 40 is defined by one wire 16' continuing in accordance with a first defined helical path way of the stent body (e.g., medial region), while a second wire 16" transitions from a second defined helical path way of the stent body in the medial region 30 into a straight portion 22 that extends in a generally axial direction in the distal end region, and further transitions back into the first helical direction distal of the straight portion. The wire 16" extends distally from the straight portion 22 whereupon it bends back proximally to join an adjacent wire 16' at a joining region 26.

Each of the various configurations of the distal end region 40 of the stent 12 shown in FIGS. 3-9 provide the endoluminal device 10 with improved distal end flexibility. Providing the distal end of the device with improved flexibility reduces the forces that the device 10 applies against the bends within wall of the pancreatic duct as the device 10 is advanced therethrough. The reduction in force function to "soften" the impact of the device 10 as it pushes against and around the walls of the duct. As a result, irritation of the duct is reduced, which in turn minimizes both immediate and potentially long term complications to the patient.

Figure 10:
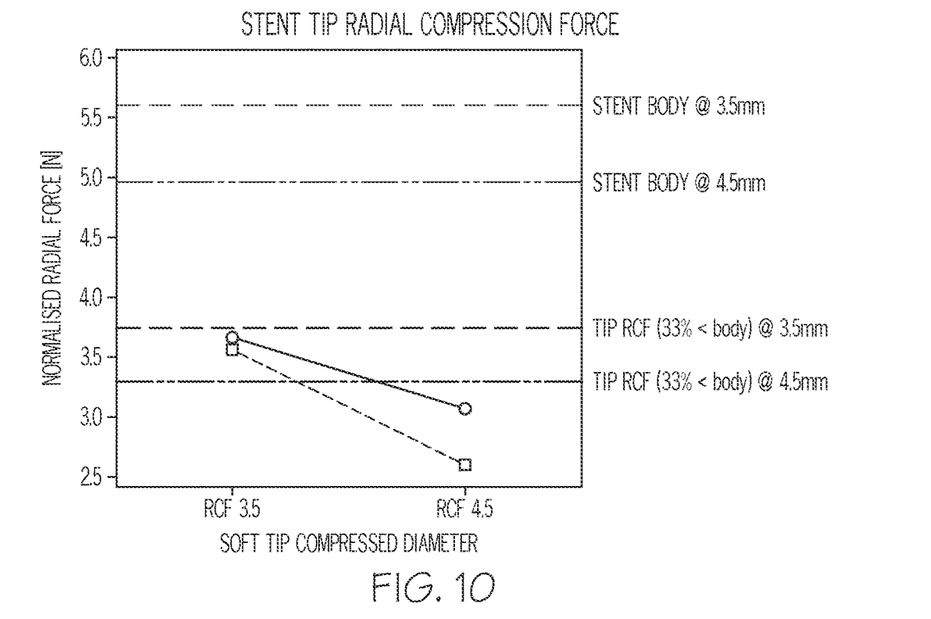
FIG. 10 is a chart showing the normalized peak force required to radially compress two examples of the endoluminal device, and showing the force difference between the medial region of the devices and the distal end region of the devices respectively.
Figure 11:
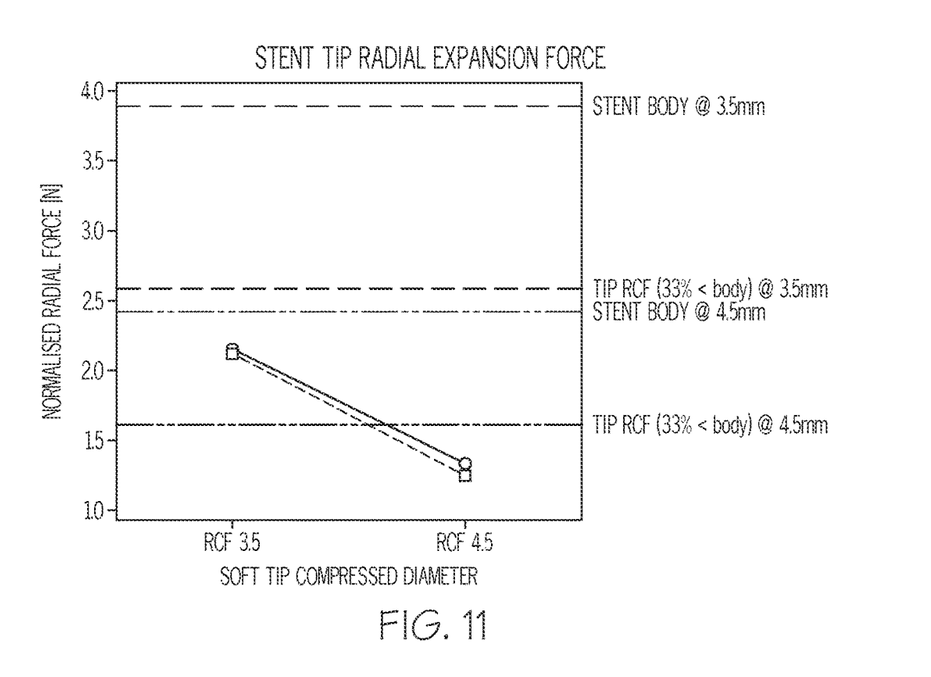
FIG. 11 is a chart showing the normalized peak force required to radially expand two examples of the endoluminal device, and showing the force difference between the medial region of the devices and the distal end region of the devices respectively.

This "softness" as characterized above is depicted in the charts shown in FIGS. 10 and 11. In FIG. 10 test results of two examples of the endoluminal device 10 are shown. The chart illustrates that normalized radial force (N) applied to the medial region 30 (STENT BODY) and the distal end region 40 (TIP) of devices 10 having a 3.5 mm reduced diameter and 4.5 mm reduced diameter respectively. As shown, regardless of the diameter of the device 10, the amount of force necessary to reduce the distal end region 40 is ~33% less than the force required to reduce the medial region 30 of the device. In other words: to radially compress the device 10 to a reduced diameter configuration, the force required to reduce the distal end region 40 is approximately two-thirds or less of the force required to radially compress the medial region 30. The stent radial force results shown in FIGS. 10-13 were measured on an MSI R-Series Radial Expansion Force Testing Equipment (commercially available from Machine Solutions, Inc. in Flagstaff, Ariz.—see, for example, "RX550 (Stents) & RX650 (Filters, Heart Valves, Grafts)," Machine Solutions, Inc., Flagstaff, Ariz., 2012, available online at http://www.machinesolutions.com/Medical-Device-Performance-Testing/Testing-Equipment/Radial-Expansion-Force-Testing-Equipment-RX550-650.htm, which is incorporated herein by reference). Radial expansion force testing may also be performed using equipment commercially available from Blockwise Engineering, LLC (Tempe, Ariz.) (see, for example, "Radial Force Testing Equipment," Blockwise Engineering, LLC, Tempe, Ariz., 2014, available online at http://www.blockwise.com/radial-force.htm, which is incorporated herein by reference).

FIG. 11 shows a similar comparison of devices 10 of different diameters, but here the devices were tested to determine the different radial force required to radially expand the devices. As shown, regardless of the diameter of the device 10 the force required to radially expand the distal end region 40 (TIP) is ~33% less than the force required to radially expand the medial region 30 of the device 10. In other words: to radially expand the device 10 to an expanded diameter configuration, the force required to expand the distal end region 40 is approximately two-thirds or less of the force required to radially expand the medial region 30.

The reduction in forces necessary to manipulate the distal end region 40 of the device 10, such as are illustrated in FIGS. 10 and 11, provide the distal end region 40 with significantly more flexibility than the medial region 30 of the device 10. This improved flexibility allows the distal end region 40 to minimally impact the pancreatic duct as the entire device 10 is advanced therethrough.

Figure 12:
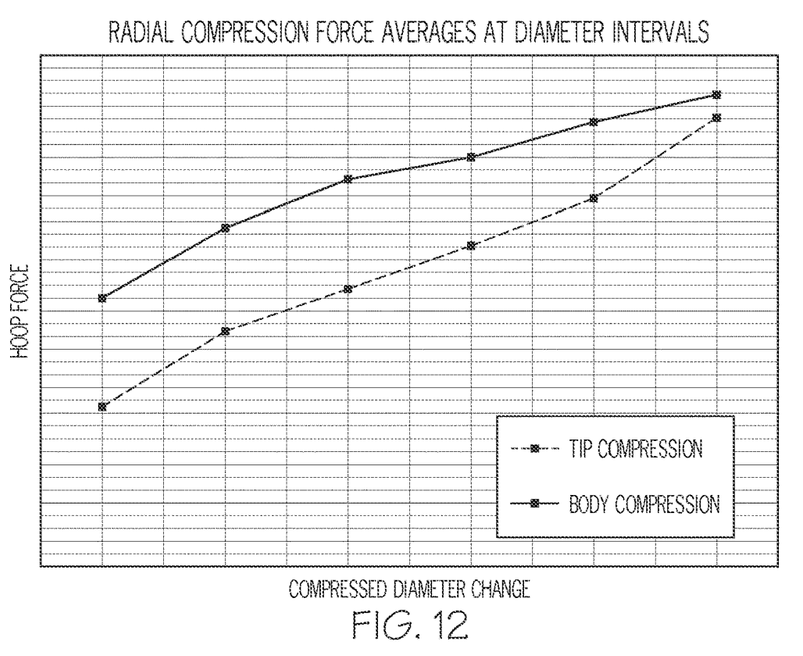
FIG. 12 is a chart showing a performance graph to demonstrate the consistently lower radial compression forces of the tip (e.g., distal end region), relative to the body (e.g., medial region), at different diameters.
Figure 13:
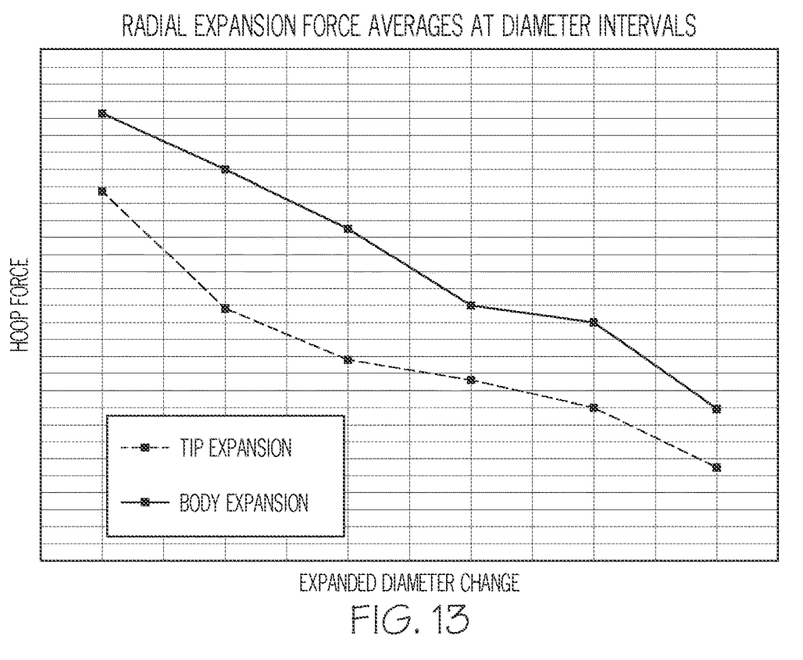
FIG. 13 is a chart showing a performance graph to demonstrate the consistently lower radial expansion forces of the tip (e.g., distal end region), relative to the body (e.g., medial region), at different diameters.

It has been determined that endoluminal devices of the present disclosure may include a characteristic wherein, when reducing the diameter of the device, radial compression forces at the tip (e.g., the distal end region) are lower than the radial compression forces at the body portion (e.g., the medial region), as shown in FIG. 12 over a wide range of diameter changes. Similarly, it has been determined that endoluminal devices of the present disclosure may include a characteristic wherein, when increasing the diameter of the device, radial expansion forces at the tip (e.g., the distal end region) are lower than the radial expansion forces at the body portion (e.g., the medial region), as shown in FIG. 13 over a wide range of diameter changes.

The various combinations of features shown and described herein, such as the presence of transitioning and/or reduced braid angles and the different structural configurations of the stent wires within the distal end region 40 of the stent 12, relative to the configuration of the medial region 30, can, in addition to reducing the expansion and reduction forces within the distal end region, affect other performance attributes of the device 10 such as, for example, longitudinal flexibility of one or more regions of the device 10, the trackability of the device, etc.

What is claimed is:

1. An endoluminal device comprising a braided stent formed of a plurality of interwoven wire segments, wherein a first portion of the wire segments extends helically in a first helical direction and a second portion of the wire segments extends helically in a second helical direction opposite the first helical direction,
    the device having a proximal end braided region, a distal end braided region, and a medial braided region extending therebetween; the distal end braided region of the device being more flexible than the medial braided region such that a radial compressive force at a reduced diameter configuration is lesser at the distal end than the medial braided region,
    wherein the distal end braided region has a diameter equal to or greater than a diameter of the medial braided region,
    wherein the distal end braided region of the device comprises a plurality of loops formed from the plurality of wire segments, each loop having a length in an axial direction and a maximum width in a circumferential direction at a widest portion of the loop, wherein the length is greater than the maximum width,
    wherein each loop is defined by a terminal end region of a first wire and a terminal end region of a second wire, the terminal end region of the first wire having a first elongated straight portion and a distal curved region between the first elongated straight portion and a terminal end of the first wire, the first wire terminating at a joining region with the terminal end region of the second wire, the terminal end region of the second wire having a second elongated straight portion terminating in the joining region with the terminal end of the first wire, the second elongated straight portion of the second wire proximal of the joining region having a length greater than the maximum width of the loop,
    wherein every wire segment that extends in the first helical direction forms the first elongated straight portion and the distal curved region of one of the loops.

2. The device of claim 1, the distal end braided region of the device being more flexible than the medial braided region such that the radial compressive force at the reduced diameter configuration at the distal end is less than about two-thirds of that at the medial region.

3. The device of claim 1, wherein the length of each loop is at least twice its maximum width.

4. An endoluminal device comprising a braided stent formed of a plurality of interwoven wire segments, wherein a first portion of the wire segments extends helically in a first helical direction and a second portion of the wire segments extends helically in a second helical direction opposite the first helical direction,
    the device having a proximal end braided region, a distal end braided region, and a medial braided region extending therebetween; the distal end braided region of the device being more flexible than the medial braided region such that a radial compressive force at a reduced diameter configuration is lesser at the distal end than the medial braided region, wherein the distal end braided region has a diameter equal to or greater than a diameter of the medial braided region, wherein the distal end braided region of the device comprises a plurality of loops formed from the plurality of wire segments, each loop having a length in an axial direction and a maximum width in a circumferential direction, wherein the length is greater than the maximum width, wherein each loop is defined by a terminal end region of a first wire and a terminal end region of a second wire, the terminal end region of the first wire having a first elongated straight portion and a distal curved region between the first elongated straight portion and a terminal end of the first wire, the first wire terminating at a joining region with the terminal end region of the second wire, the terminal end region of the second wire having a second elongated straight portion terminating in the joining region with the terminal end of the first wire, the second elongated straight portion of the second wire proximal of the joining region having a length greater than the maximum width of the loop, wherein every wire segment that extends in the first helical direction forms the first elongated straight portion and the distal curved region of one of the loops, wherein the plurality of interwoven wire segments form:
a medial braided region braid pattern in the medial braided region wherein the plurality of interwoven wire segments define a medial braided region braid angle; and
a distal end braided region braid pattern in the distal end braided region wherein the plurality of interwoven wire segments define a distal end braided region braid angle, the medial braided region braid angle having a value greater than that of the distal end braided region braid angle in at least a resting state, wherein the medial braided region having the medial braided region braid angle has an outer diameter the same as the distal end braided region having the distal end braided region braid angle.

5. The device of claim 4, wherein the medial braided region braid angle is greater than 90 degrees.

6. A stent, comprising:
a tubular framework having a first end region, a second end region, and a medial region between the first and second end regions, the tubular framework comprising a plurality of interwoven filaments including a plurality of first filament portions and a plurality of second filament portions;
the first filament portions extending helically along the medial region of the tubular framework in a first helical direction;
the second filament portions extending helically along the medial region of the tubular framework in a second helical direction opposite the first helical direction;
wherein an entirety of the first end region has a diameter equal to or greater than a diameter of an entirety of the medial region, wherein the first end region includes a plurality of loops formed from the plurality of filaments, wherein every end of the plurality of filaments in the first end region forms one of the plurality of loops, wherein each of the plurality of loops has a length in an axial direction of the tubular framework and a maximum width in a circumferential direction at a widest portion of the loop of the tubular framework, wherein the length is greater than the maximum width, wherein each loop of the plurality of loops is formed with an end region of one of the first filament portions joining an end region of one of the second filament portions at a joining region in which terminal ends of the first and second filament portions terminate at the joining region, wherein the end region of each of the first filament portions includes a first elongated straight portion extending in the axial direction, a second elongated straight portion extending in the axial direction parallel to the first elongated straight portion, and a curved portion extending between the first elongated straight portion and the second elongated straight portion, wherein every first filament portion extending in the first helical direction forms the first elongated straight portion, the second elongated straight portion, and the curved portion of one of the loops, such that the first elongated straight portion of each loop contacts an adjacent loop, wherein the end region of each of the second filament portions is a third elongated straight portion extending in the axial direction parallel to the first and second elongated straight portions, the third elongated straight portion having a length measured from the joining region toward the medial region which is greater than the maximum width of the loop.

7. The stent of claim 6, wherein the second elongated straight portion extends toward the second end region from the curved portion adjacent to the third elongated straight portion.

8. The stent of claim 6, wherein the length of each loop is at least twice its maximum width.

* * * * *